(12) United States Patent
Lestoquoy (10) Patent No.: US 10,945,747 B2
(45) Date of Patent: Mar. 16, 2021

(54) SYSTEM FOR TREATING AN EPISTAXIS

(71) Applicant: Vygon, Ecouen (FR)

(72) Inventor: Patrick Lestoquoy, Attiches (FR)

(73) Assignee: Vygon

( * ) Notice: Subject to any disclaimer, the term of this patent is extended or adjusted under 35 U.S.C. 154(b) by 280 days.

(21) Appl. No.: 15/761,645

(22) PCT Filed: Sep. 21, 2016

(86) PCT No.: PCT/EP2016/072419
§ 371 (c)(1),
(2) Date: Mar. 20, 2018

(87) PCT Pub. No.: WO2017/050823
PCT Pub. Date: Mar. 30, 2017

(65) Prior Publication Data
US 2018/0353197 A1      Dec. 13, 2018

(30) Foreign Application Priority Data

Sep. 21, 2015  (FR) ...................................... 1558872
Jan. 11, 2016  (FR) ...................................... 1650205

(51) Int. Cl.
*A61B 17/24* (2006.01)
*A61B 17/12* (2006.01)
*A61B 17/00* (2006.01)

(52) U.S. Cl.
CPC .......... *A61B 17/24* (2013.01); *A61B 17/1204* (2013.01); *A61B 17/1219* (2013.01);
(Continued)

(58) Field of Classification Search
CPC ................ A61F 13/2005; A61F 13/126; A61F 13/2022; A61F 13/20; A61F 2013/00476;
(Continued)

(56) References Cited

U.S. PATENT DOCUMENTS 6,517,509 B1     2/2003  Shippert
2002/0055701 A1* 5/2002  Fischell .................. A61L 31/16
                                                                        602/47
(Continued)

FOREIGN PATENT DOCUMENTS

JP     2004515300 A        5/2004
WO    WO 02/47558   *    11/2001
WO    2005053589 A1       6/2005

OTHER PUBLICATIONS

International Search Report for PCT/EP2016/072419 dated Dec. 2, 2016.
French Search Report for FR1558872 dated Jun. 6, 2016.

*Primary Examiner* — Katherine M Shi
(74) *Attorney, Agent, or Firm* — Lerner, David, Littenberg, Krumholz & Mentlik, LLP (57) ABSTRACT

The invention relates to a system for treating an epistaxis, comprising: a compressible body designed to come into contact with walls of a nasal cavity of a patient, or surrounded by a veil of hemostatic properties; an envelope designed to envelop the compressible body; and a compression device for compressing the compressible body in the envelope, said compression device being designed so as to compress or release the compressible body.

18 Claims, 5 Drawing Sheets

(52) U.S. Cl.
CPC .. *A61B 17/12104* (2013.01); *A61B 17/12159* (2013.01); *A61B 2017/00849* (2013.01); *A61B 2017/00862* (2013.01); *A61B 2017/00867* (2013.01); *A61B 2017/00893* (2013.01); *A61B 2017/1205* (2013.01); *A61B 2017/246* (2013.01); *A61B 2217/005* (2013.01)

(58) Field of Classification Search
CPC ........ A61F 13/2051; A61F 2013/00463; A61F 13/2028; A61F 13/2074; A61F 2007/0006; A61F 13/2057; A61F 13/00463; A61B 17/24; A61B 17/12104; A61B 17/1219; A61B 2017/12004; A61B 17/12022; A61B 17/12159; A61B 17/12; A61B 2017/00893; A61B 17/1204; A61B 2017/1205; A61B 2017/246; A61B 17/12136; A61B 17/12099; A61B 17/12131; A61B 17/0057
See application file for complete search history.

(56) References Cited

U.S. PATENT DOCUMENTS

| | | |
|---|---|---|
| 2004/0073299 A1 | 4/2004 | Hudson et al. |
| 2004/0153120 A1* | 8/2004 | Seifert ............. A61B 17/12159 606/200 |
| 2014/0276627 A1 | 9/2014 | Jenkins et al. |
| 2016/0030050 A1* | 2/2016 | Franano ........... A61B 17/12031 606/195 |

\* cited by examiner

SYSTEM FOR TREATING AN EPISTAXIS

CROSS REFERENCE TO RELATED APPLICATIONS

The present application is a national phase entry under 35 U.S.C. § 371 of International Application No. PCT/EP2016/072419, filed Sep. 21, 2016, published in French, which claims priority from French Patent Application Nos. 1650205 filed Jan. 11, 2016 and 1558872 filed Sep. 21, 2015, all of which are incorporated herein by reference.

FIELD OF THE INVENTION

The invention relates to the field of medical devices for controlling a nasal flow or a hemorrhage of the nasal cavities (or epistaxis).

TECHNOLOGICAL BACKGROUND

An epistaxis is a flow of blood originating in the nasal cavities. This bleeding is very frequent and benign most of the time. In certain cases, however, it can become, due to its abundance, its repetition or the fragility of the site, a true medical-surgical emergency.

Systems suitable for absorbing the blood and carrying out vasoconstriction by compression against the walls of the nasal cavities have thus been proposed that are introduced into the nasal cavity of the patient, so as to treat these epistaxis.

For example, there exist wicks having hemostatic properties and made of an expansible material configured to fill the nasal cavity. Typically, the wicks can be made of oxidized regenerated cellulose, and therefore be hemostatic per se, or of an expansible, non-hemostatic material, such as polyvinyl alcohol. However, such wicks are traumatizing upon introduction and withdrawal, despite their possible re-humidification prior to withdrawal. Moreover, there is a considerable risk of secondary hemorrhage due to the poorly controlled pullout of the wick remaining at the junction point of the hemostasis.

Also known are inflatable balloon systems comprising a first configuration, in which the balloon is deflated so as to be inserted in the nasal cavity, and a second configuration in which the balloon is inflated so as to apply pressure against the nasal cavity and stop the hemorrhage. However, these systems are particularly uncomfortable for the patient due to the considerable pressure applied by the balloon so as to stop the hemorrhage, knowing that this pressure is often greater than necessary to guarantee that the balloon adapts to the physiognomy of the nasal cavity of the patient. Moreover, these systems do not have a rapid hemostatic effect. Moreover, these systems comprising a balloon are flexible and therefore difficult to introduce and to position with accuracy in a nasal cavity of a patient.

In addition, known from document U.S. Pat. No. 6,517,509 is a treatment system for epistaxis which comprises an expansible wick and a groove for introducing said wick into the nasal cavity. However, such a device does not allow either controlling the pressure exerted on the walls of the nasal cavity or avoiding a secondary hemorrhage at the time of withdrawal of the wick. It is also noted that the introduction of the wick into the nasal cavity is difficult in that it is not guided by the introducing groove.

Known moreover from document WO 2005/053589 is a system for removing organic fluid from a body which allows easy recovery of a hemostatic wick. However, such a device does not allow either controlling the pressure exerted on the walls of the zone of the body to be blotted, or withdrawing the wick in a controlled and non-traumatic manner. This system is also not suitable for the introduction of a wick into a nasal cavity.

Known, finally, from document US 2014/0276627 is a nasal suction system for fluid which allows blotting a nasal passage using an expansible wick. However, such a device does not allow controlling the pressure exerted on the walls of the passage or withdrawing the wick from the cavity non-traumatically.

SUMMARY OF THE INVENTION

One objective of the invention is therefore to propose a system for treating an epistaxis which makes it possible to stop a nasal hemorrhage without risk of secondary hemorrhage at the junction point of the hemostasis by applying a controlled pressure on the walls of a nasal cavity of a patient, and which is further simple to implement while still being more ergonomic and less traumatizing for the patient than the systems of the prior art.

For this purpose, the invention proposes a system for treating an epistaxis comprising:
a compressible member with shape memory having a compressed configuration, in which the compressible member is compressed and is configured to be introduced into a nasal cavity of a patient, and an expanded configuration, in which the compressible member is deployed and is configured to come into contact with walls of the nasal cavity of the patient,
an envelope configured to envelop the compressible member, and
a device for compressing the compressible member in the envelope, said compression device being configured to bring the compressible member into its compressed or deployed configuration.

Certain preferred but not limiting features of the system described above are the following, taken individually or in combination:
the compression device comprises an implantation tube, configured to be introduced into the nasal cavity of a patient, said implantation tube having a proximal end, a distal end and a central through passage extending between the proximal end and the distal end, and said compressible member being configured to be housed in the central passage of the implantation tube in the compressed configuration, and a fastener configured to be attached to the envelope and protrude from the proximal end of the implantation tube when the compressible member is housed in the central passage, in order to facilitate the introduction of the compressible member and of the envelope into the implantation tube when the compressible member is in the expanded configuration,
the envelope comprises a net or a film.
The envelope is configured to hermetically enclose the compressible member so as to form a sealed enclosure, and the compression device is configured to reduce a pressure in the assembly formed by the compressible member enclosed in the envelope so as to bring the compressible member into its compressed configuration,
the envelope comprises a flexible film,
the envelope comprises a polyethylene film and/or a polyurethane film, said envelope being able to have a thickness comprised between a few microns and a hundred microns, the compression device comprises a syringe or a partial vacuum member, the compressible member has a proximal end in proximity to which is attached the compression device and a distal end opposite to the proximal end, a central recess being formed between the proximal end and the distal end of the compressible member and the system further comprising a tube housed in the central recess, the tube is configured to be put into fluid communication with the compression device in order to reduce the pressure in the compressible member, through openings being formed in the tube between the proximal end and the distal end of the compressible member in order to allow progressive compression and expansion of the compressible member over its entire length, the system further comprises a lock comprising a first attachment member attached to a proximal end of the tube and a second complementary attachment member attached to the compression device, the tube protrudes from the compressible member and comprises a fin configured to be attached to a zone of the body of a patient and/or the system further comprises a veil, having hemostatic properties, covering the envelope, said veil being able to comprise a nonwoven veil having an acid pH to impart hemostatic properties thereto.

According to a second aspect, the invention proposes an assembly for treating an epistaxis, comprising:

a compressible member having a compressed configuration, wherein the compressible member is compressed and is configured to be introduced into a nasal cavity of a patient, and an expanded configuration, in which the compressible member is deployed and is configured to come into contact with walls of the nasal cavity of the patient, and an envelope, said envelope surrounding the compressible member and being attached to said compressible member so as to form a sealed enclosure.

This assembly is configured to be implemented in a system for treating an epistaxis as described above.

According to a third aspect, the invention also proposes a system for treating an epistaxis, comprising:

an implantation tube, configured to be introduced into a nasal cavity of a patient, said implantation tube having a proximal end, a distal end and a central through passage extending between the proximal end and the distal end, a compressible member having hemostatic properties, said compressible member having a compressed configuration, in which the compressible member is compressed and is configured to be housed in the central passage of the implantation tube, and an expanded configuration, in which the compressible member is deployed and is configured to come into contact with walls of the nasal cavity of the patient, an envelope configured to envelop the compressible member, and a fastener configured to be attached to the envelope and extend out of the proximal end of the implantation tube when the compressible member is housed in the central passage, in order to facilitate the introduction of the compressible member into the implantation tube when the compressible member is in the expanded configuration.

Certain preferred but non-limiting features of the system for treating an epistaxis according to the third aspect of the invention are the following, taken individually or in combination:

the fastener is configured to extend in the central passage and protrude from the proximal end of the implantation tube when the compressible member and the envelope are at least partially housed in the implantation tube, the fastener comprises at least one strand or an instrument containing a hook or a gripper, the envelope comprises a net, the net comprises a material having anti-coagulation properties, the compressible member comprises a foam, for example an oxidized regenerated cellulose foam having hemostatic properties, a foam made of a material not having hemostatic properties enveloped in a veil made of an oxidized regenerated cellulose having hemostatic properties or even a foam made of a material having no hemostatic properties soaked with a fluid having hemostatic properties, the envelope comprises a film, the system further comprises a veil having hemostatic properties covering the envelope, said veil being able to comprise a nonwoven veil having an acid pH to impart hemostatic properties thereto, the compressible member and the implantation tube have an overall cylindrical shape, preferably a cylinder of revolution, the system further comprises a catheter and the compressible member has a central recess configured to receive said catheter sliding, the catheter comprises a proximal end configured to be put into fluid communication with a fluid reservoir, and a distal end, opposite to the proximal end and in which is formed an injection opening, said injection opening being in fluid communication with the proximal end, and/or the system further comprises a mandrel configured to be housed in the implantation tube so as to press the compressible member from the distal end of the implantation tube and thus allow the withdrawal of the implantation tube.

According to a fourth aspect, the invention also proposes an assembly for treating an epistaxis comprising:

a compressible member having hemostatic properties, said compressible member having a compressed configuration, in which the compressible member is compressed and is configured to be housed in the central passage of the implantation tube of a system according to the third aspect of the invention, and an expanded configuration, in which the compressible member is deployed and is configured to come into contact with walls of the nasal cavity of the patient, an envelope configured to envelop the compressible member, and a fastener configured to be attached to the envelope and protrude from the proximal end of the implantation tube when the compressible member is housed in the central passage, in order to facilitate the introduction of the compressible member and the envelope into the implantation tube when the compressible member is in the expanded configuration.

BRIEF DESCRIPTION OF THE DRAWINGS

Other features, aims and advantages of the present invention will be better understood upon reading the detailed description that follows, and referring to the appended drawings given by way of non-limiting examples and in which.

DETAILED DESCRIPTION OF AN EMBODIMENT

Hereafter, "proximal" will designate a portion which is situated in proximity to the operator when he is using the system of the invention.

In order to ensure stopping an epistaxis in a nasal cavity of a patient, the invention proposes a system 1 for treating an epistaxis comprising:

a compressible member 20, 120 having a compressed configuration, in which the compressible member 20, 120 is compressed and is configured to be introduced into a nasal cavity of a patient, and an expanded configuration, in which the compressible member 20, 120 is deployed and is configured to come into contact with walls of the nasal cavity of the patient, an envelope 30, 130 configured to envelop the compressible member 20, 120, and a device 10, 110 for compressing the compressible member 20, 120 in the envelope 30, 130, said compression device 10, 110 being configured to bring the compressible member 20, 120 into its compressed or deployed configuration.

The compressible member 20, 120 has a shape suitable for adjusting itself, in the expanded configuration, to the shape of the nasal cavity of the patient. For example, the compressible member 20, 120 can have a substantially cylindrical shape (with a square, parallelepiped, oval, round, etc. cross section), or a cylinder or revolution, or as a variant have a non-uniform section between its distal end 24, 124 and its proximal end 22, 122. Typically, the compressible member 20, 120 can have a narrower distal portion and an enlarged proximal portion.

In the expanded configuration, the compressible member 20, 120 has a periphery having an average width L comprised between twenty and forty millimeters. By peripheral width L is meant here the distance between two parallel straight lines (or "support lines") which are tangent to the closed curve formed by the periphery of the sensor at two distinct points. For example, for a cylinder-of-revolution compressible member 20, 120 20, the average width L is equal to the outer diameter of the cylinder.

The compressible member 20, 120 can in particular be made of a compressible material with shape memory such as a foam, which can in particular have a density of 25 kg/m³.

Unlike the prior art systems implementing an inflatable balloon, the compressible member 20, 120 of the invention is in the expanded configuration when it is at rest. The pressure applied by the compressible member 20, 120 is therefore easy to control and results from the material selected to manufacture it.

The envelope 30, 130 can have the shape of a planar sheet and be enveloped around the compressible member 20, 120. As a variant, the envelope 30, 130 can have the general shape of a conformal sleeve so as to be able to be adjustably slipped on the compressible member 20, 120. In particular, the dimensions of the envelope 30, 130 shaped like a sleeve can be adjusted to the dimensions and to the shape of the compressible member 20, 120 so as to limit the formation of creases, which would form excess thicknesses likely to create discomfort for the patient. For example, for a compressible member 20,120 with a cylinder-of-revolution shape in the expanded configuration, the envelope 30, 130 can have a cylinder-of-revolution shape of which the outer diameter is substantially equal to the outer diameter of the compressible member 20.

The compression device 10, 110 can comprise a member 10 configured to compress, from the outside, the compressible member so as to easily introduce and withdraw it from a nasal cavity of a patient (first embodiment). The compression device 10, 110 can otherwise comprise a member 110 configured to compress, from the inside (by aspiration of air into the compressible member 120), the compressible member 120 (second embodiment).

First Embodiment: Compression By the Outside of the Compressible Member

In this first embodiment, illustrated with reference to FIGS. 1 to 5, the compression device comprises an implantation tube 10, configured to be introduced into the nasal cavity of the patient, said implantation tube 10 having a proximal end 12, a distal end 14 and a central through passage 16 extending between the proximal end 12 and the distal end 14. Moreover, the compressible member 20 has hemostatic properties. Finally, the system further comprises a fastener 40 configured to be attached to the envelope 30 and protrude from the proximal end 12 of the implantation tube 10 when the compressible member 20 is housed in the central passage 16, in order to facilitate the introduction of the compressible member 20 and the envelope 30 into the implantation tube 10 when the compressible member 20 is in the expanded configuration.

Figure 1:
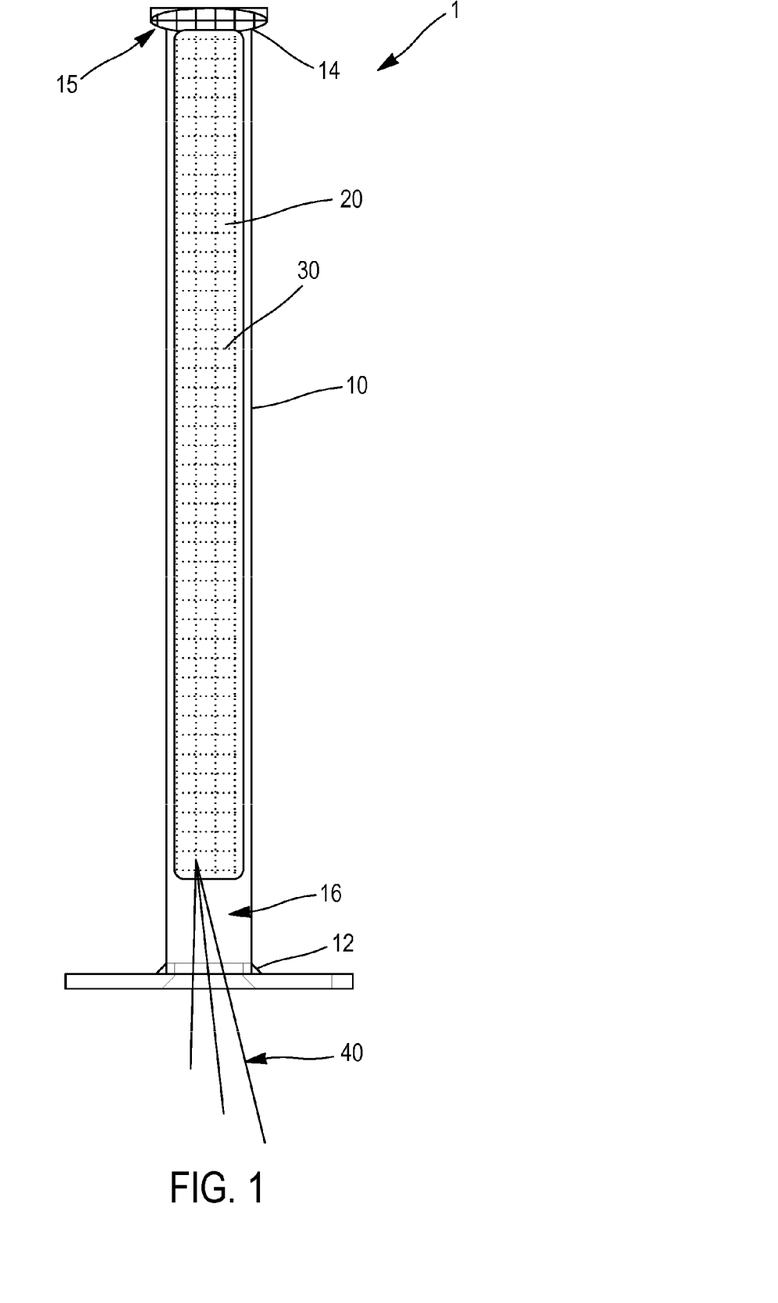
FIG. 1 is a longitudinal section view of an exemplary embodiment of a system for treating an epistaxis conforming to a first embodiment of the invention.

The compressible member 20 can in particular be made of a compressible material with shape memory such as foam, typically an oxidized regenerated cellulose foam having hemostatic properties, an inert foam—that is made of a material not having hemostatic properties—enveloped in a veil made of oxidized regenerated cellulose having hemostatic properties, or an inert foam soaked with a fluid having hemostatic properties. In one embodiment, the compressible member 20 comprises a polyurethane foam having a density of 25 kg/m³ having open cells enveloped in a nonwoven fabric having an acid pH to impart hemostatic properties on the compressible member 20. In another exemplary embodiment, the compressible member 20 comprises an oxidized regenerated cellulose sponge which has hemostatic properties. In this case, in order to guarantee that the sponge 20 can adopt a compressed configuration and an expanded configuration, the cellulose sponge 20 can in particular be treated using a plasticizer, such as magnesium chloride salts.

The envelope 30 has as its objective to allow, using the fastener 40, the reintroduction of the compressible member 20 into the implantation tube 10, when the compressible member 20 is in the expanded configuration.

In a first embodiment, the envelope 30 comprises a net. The net 30 has a sufficiently large mesh to allow the accomplishment of hemostasis in the nasal cavity, but sufficiently small to ensure the retention of the compressible member 20 during its introduction into the nasal cavity. Typically, the net 30 can have meshing comprising mesh having a dimension comprised between two and five millimeters.

The net 30 can be made of an inert material.

As a variant, the net 30 can be chemically treated so as to have anti-coagulant properties. In this manner, the anticoagulant treatment allows the adhesion of the net 30 to the walls in the discrete zones of the wall against which the net 30 is in contact to be limited, and therefore facilities the withdrawal of the compressible member 20 in a less traumatizing manner for the patient.

In a second embodiment, the envelope 30 comprises a flexible film.

Preferably, the envelope 30 is made in a non-elastic material. For example, the envelope 30 can be made of polyamide, of polyethylene or of polyurethane.

The fastener 40 can be formed integrally with the envelope 30 or applied and attached to the envelope 30.

Figure 2:
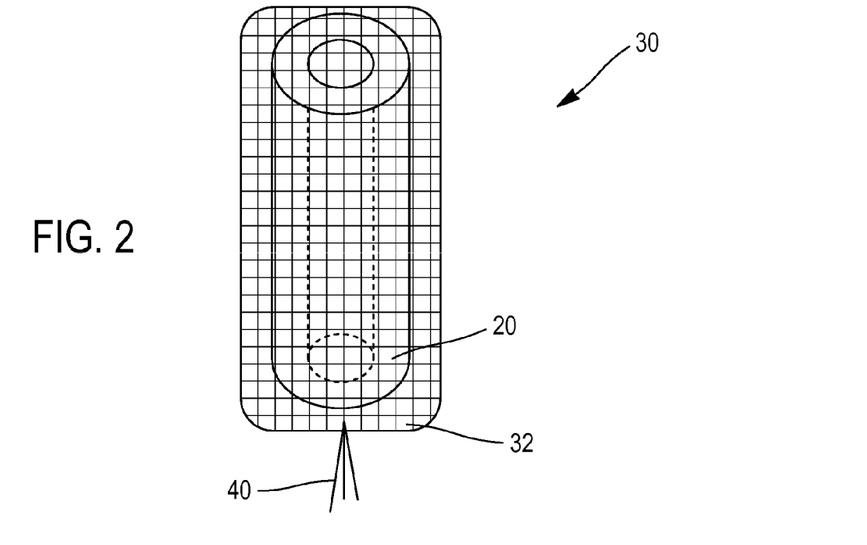
FIG. 2 is a perspective view of an exemplary embodiment of a compressible member enveloped in a system conforming to the first embodiment of the invention.
Figure 3:
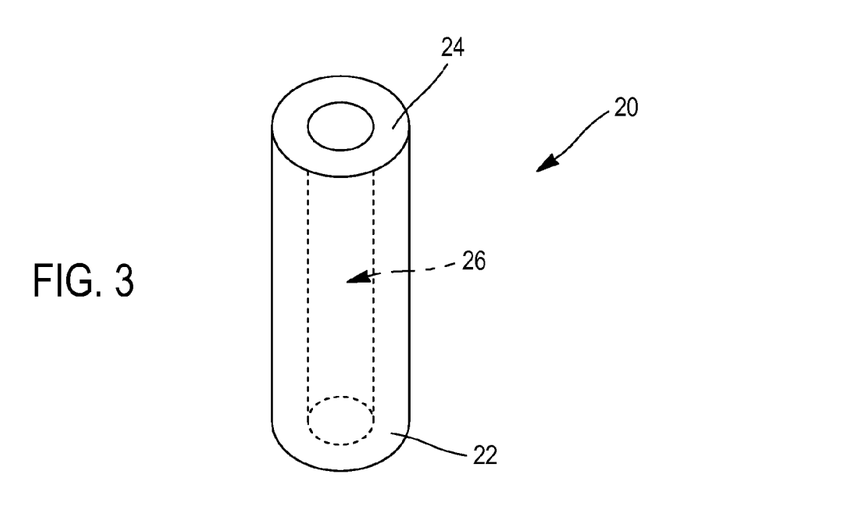
FIG. 3 is a perspective view of the compressible member of FIG. 2.

In one exemplary embodiment, as can be seen in FIG. 2, the fastener 40 can comprise one or more flexible strands, attached to the proximal end 32 of the envelope 30.

As a variant, the fastener 40 can comprise a rigid instrument comprising a hook or a gripper attached to the free end of a rigid stem which can be made of metal or of a plastic material. In the case where the envelope 30 comprises a net, the hook or the gripper of the instrument can then be introduced into one or more meshes of the net 30 while its proximal end 32 remains accessible to an operator at the proximal end 12 of the implantation tube 10.

Regardless of the embodiment, tension using the fastener 40 on the envelope 30, which surrounds the compressible member 20, allows the compressible member 20 to be progressively detached from the walls of the nasal cavity and to bring it progressively into the compressed configuration from its proximal end 22 to its distal end 24 thanks to its reintroduction into the implantation tube 10. Unlike conventional wicks, the compressible member 20 is therefore peeled little by little, and not detached in a single block from the walls of the cavity, thus reducing the trauma to which the patient is subjected. Once the compressible member 20 is completely introduced into the implantation tube 10, this is located in the compressed configuration, in which its bulk is reduced. The extraction of the compressible member 20 is therefore easier for an operator and more comfortable for the patient than in the prior art, where the wicks are extracted when they are soaked with blood and have maximum bulk.

The implantation tube 10 has a substantially cylindrical shape, for example a cylinder of revolution.

The distal end 14 of the implantation tube 10 can be flared 15 in order to facilitate the reintroduction of the compressible member 20 to ensure its progressive compression.

The proximal end 12 of the implantation tube 10 can comprise a handle equipped with a guard.

The inner diameter of the central passage 16 can be comprised between six and twelve millimeters.

If required, the implantation tube 10 can have, at its periphery, graduations or markings in order to facilitate is positioning in the nasal cavity.

Figure 4:
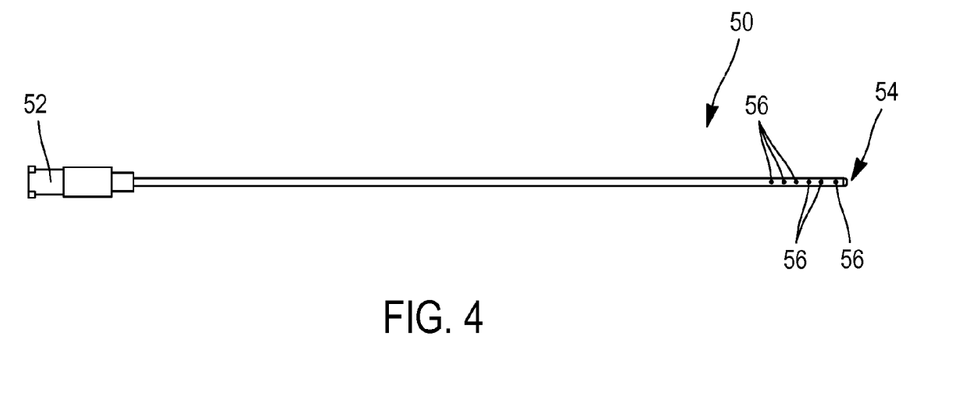
FIG. 4 is a side view of an exemplary embodiment of a catheter which can be used in a treatment system conforming to the first embodiment of the invention.

Optionally, the system 1 can further comprise a catheter 50. The catheter 50 can in particular allow re-humidification of the compressible member 20 and/or the injection of an anesthetic product into the nasal cavity before withdrawing the compressible member 20 from the nasal cavity. To this end, the compressible member 20 can in particular comprise a central through recess 26, extending between the proximal end 22 and the distal end 24 of the member 20 and configured to slidably receive the catheter 50. In the case of a cylinder-of-revolution compressible member 20, the central recess 26 extends parallel to the axis of revolution of the compressible member 20.

The catheter 50 can comprise a proximal end 52, configured to be put into fluid communication with a fluid reservoir, and a distal end 54, opposite to the proximal end 52 and designed to be introduced into the central recess 26 of the compressible member 20. The catheter 50 can be of the single opening type and comprise a central through opening extending between its proximal end 52 and its distal end 54, or as a variant be of the multi-opening type and comprise several through openings.

In one embodiment, the catheter 50 is of the single-opening type and comprises an injection opening 56 at its distal end 54. Such a catheter 50 then allows the injection of an anesthetic product prior to the installation of the compressible member 20 and/or the injection of a product to soften the compressible member 20 prior to its withdrawal.

Alternatively or as a complement, the catheter 50 can be of the single opening type and comprise several injection openings 56 formed at its periphery and distributed between its distal end 54 and its proximal end 52 in order to allow the injection of a fluid along the central recess 26 of the compressible member 20.

Optionally, the catheter 50 can be equipped with graduations or colorimetric markers in order to allow its accurate positioning in the compressible member 20. For example, the catheter 50 can comprise graduations or markers at regular intervals, typically every centimeter, over a segment adjacent to its distal end 54 or over its entire length.

The catheter 50 can then be used in order to inject a product having hemostatic properties into the compressible member 20 prior to its implantation in the nasal cavity, in particular when the compressible member 20 is made of a material not having such properties. In this case, a catheter 50 provided on its periphery with a series of injection openings 56 distributed over a segment adjacent to its distal end 54 makes it possible to effectively and controllably soak the compressible member 20.

The system 1 for treating an epistaxis conforming to this first embodiment can then be implemented as follows.

In a first embodiment, the system 1 for treating an epistaxis can be supplied as a kit. The system 1 must then be assembled prior to its use.

To this end, a compressible member 20 is first of all enveloped or introduced into an envelope 30. At this assembly step, the compressible member 20 is in the deployed configuration.

The envelope 30 can be pre-equipped with a fastener 40. As a variant, a fastener 40 can be attached to the envelope 30.

The assembly formed by the compressible member 20, the envelope 30 and the fastener 40 is then introduced into an implantation tube 10. For example, the fastener 40 can be introduced into the implantation tube 10 by its distal end 14, then the compressible member 20—which is then in the deployed configuration—is compressed and progressively introduced with the envelope 30 into the implantation tube 10 by its distal end 14 by applying a tension force on the fastener 40 from the proximal end 12 of the implantation tube 10. Once the compressible member 20 is completely introduced into the implantation tube 10, this is then in its compressed configuration.

Figure 5:
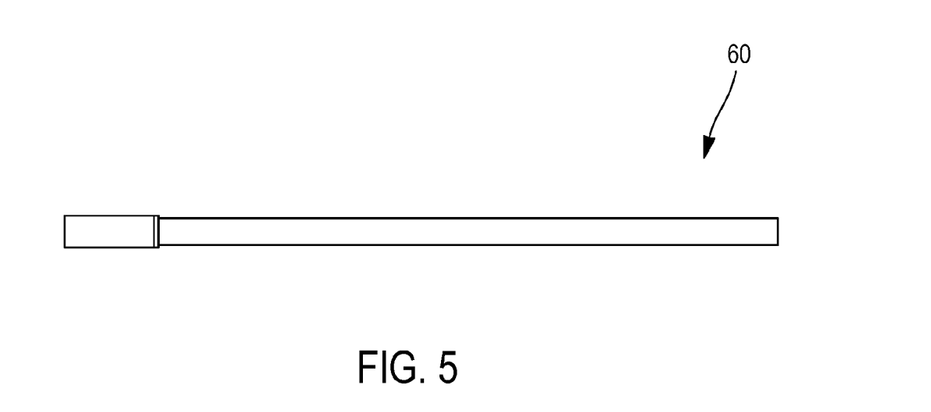
FIG. 5 is a side view of an exemplary embodiment of a mandrel which can be used with a treatment system conforming to the first embodiment of the invention.

As a variant, the compressible member 20 and the fastener 40 can also be introduced into the implantation tube 10 by its proximal end 12. In this case, the compressible member 20 and the fastener 40 can then be moved and brought into position for use in the implantation tube 10 using a mandrel 60.

In a second embodiment, the system 1 can be partially pre-assembled, the compressible member 20 being enveloped in the envelope 30 but separated from the implantation tube 10. In this case, the assembly formed by the compressible member 20, the envelope 30 and the fastener 40 is simply introduced and brought into position for use in an implantation tube 10, in a manner similar to the first embodiment.

In a third embodiment, the system 1 can be pre-assembled ready for use, the compressible member 20 being enveloped in the envelope 30 on which is attached the fastener 40 and housed in the implantation tube 10. Here, the compressible member 20 is therefore in its compressed configuration.

When the envelope 30 comprises a net, the outer surface of the compressible member 20 preferably has hemostatic properties prior to its implantation in the nasal cavity of a patient. To this end, the compressible member 20 can for example be made of a material having such properties (the case for example of a compressible member 20 comprising oxidized regenerated cellulose). As a variant, the compressible member 20 can be soaked using a fluid having these hemostatic properties. In the latter case, once the compressible member 20 is introduced into the implantation tube 10, a catheter 50 comprising at least one injection opening can be inserted into the recess of the compressible member 20 through the implantation tube 10 so as to inject the fluid into the compressible member 20. According to yet another variant, the compressible member 20 can be enveloped in a veil having hemostatic properties, such as a nonwoven veil having an acid pH to impart hemostatic properties thereto, of the Surgicel® type. The veil having hemostatic properties is then placed between the compressible member 20 and the net 30.

When the envelope 30 comprises a film, a veil having hemostatic properties of the Surgicel® type is placed around the film 30 enveloping the compressible member 20 prior to their introduction into the implantation tube 10. As a variant, the veil having hemostatic properties can be placed around the implantation tube, during the first step described hereafter.

The compressible member 20 can then comprise an inert foam.

Then, during a first step, the implantation tube 10 is brought and placed in the nasal cavity of the patient, so that its distal end 14 is placed at the epistaxis. If necessary, the operator can use possible markings or graduations present on the implantation tube 10 in order to facilitate its positioning in the nasal cavity.

During a second, optional step, a hemostatic agent (in the form of a fluid) can be injected into the nasal cavity of the patient. To that end, when the compressible member 20 comprises a central recess 26, a catheter 50 having a distal injection opening 56 can be introduced into the central passage 16 of the implantation tube 10 and into the central recess 26 of the compressible member 20 and positioned so that its injection opening 56 is situated facing the nasal cavity. The hemostatic agent can then be injected. The catheter 50 can then be withdrawn from the implantation tube 10.

As a variant, an analgesic product (local anesthetic) can also be injected using a syringe previously during the first step of introduction of the implantation tube 10 into the nasal cavity.

According to yet another variant, the analgesic product can be injected into the compressible member 20, either prior to its introduction into the implantation tube 10, or when the compressible member 20 is compressed into said implantation tube 10, (the injection then possibly being carried out using the catheter 50).

During a third step, the compressible member 20, enveloped in the envelope 30 and if necessary in the veil having hemostatic properties, can be implanted in the nasal cavity.

To this end, the compressible member 20 is brought into a zone adjacent to the distal end 14 of the implantation tube 10, as can be seen in FIG. 1. If necessary, in this position, the compressible member 20 begins to deploy at the flared end 15 of the implantation tube 10. It will be noted that in one embodiment, the compressible member 20 can be placed from the beginning in this position, prior to the step of introduction of the implantation tube 10.

A mandrel 60 can then be implemented so as to retain the compressible member 20 in position while simultaneously the implantation tube 10 is progressively extracted from the nasal cavity. For this purpose, the mandrel 60 is introduced into the implantation tube 10 by its proximal end 12 and pushed until it comes into contact with the compressible member 20. It will be noted that, during this manipulation, the distal end 14 of the installation instrument remains fixed with respect to the nasal cavity, in order to guarantee the positioning of the compressible member 20. An operator can then continue to push on the mandrel 60 and simultaneously pull on the implantation tube 10, so as to extract the compressible member 20 from the distal end 14 and to withdraw the implantation tube 10 from the nasal cavity. In this manner, the compressible member 20 is extracted progressively from the implantation tube 10, the portion of the compressible member 20 extending out from the distal end 14 of the implantation tube 10 deploying progressively in the nasal cavity.

When the totality of the compressible member 20 is extracted from the implantation tube 10, the compressible member 20, surrounded by the envelope 30 and if necessary by the veil having hemostatic properties, is then positioned with accuracy in the nasal cavity and in the expanded configuration. In fact, the position of the compressible member 20 is determined by the position of the distal end 14 of the implantation tube 10 at the beginning of the third step, which can be precisely adjusted without the risk of injuring the patient.

It will be noted that this progressive expansion also reduces the trauma to which the patient is subjected, the compressible member 20 never being moved at any time.

Moreover, by adopting its expanded configuration, the compressible member 20, which is enveloped in the envelope 30 and if necessary the veil having hemostatic properties, comes into contact with the walls of the nasal cavity.

In one variant embodiment, the mandrel 60 can comprises a central opening in order to allow the operator to leave a catheter 50 in place, in the compressible member 20, despite the withdrawal of the implantation tube 10.

The mandrel 60 and the implantation tube 10 can then be withdrawn from the nasal cavity.

If necessary, when the fastener 40 is removable, it can be detached from the envelope 30 so as not to inconvenience the patient.

As a variant, the fastener 40 can be left in place.

A hemostatic phenomenon can then take place, thanks to the hemostatic properties of the compressible member 20 or, as a variant, of the hemostatic veil that surrounds it.

At the end of the hemostatic phenomenon, the compressible member 20 and the envelope 30 can then be withdrawn.

For this purpose, during a fourth step, the implantation tube 10 can be re-introduced into the nasal cavity until it comes into abutment against the proximal end 22 of the compressible member 20. If necessary, the fastener 40 is attached to the envelope 30.

The fastener 40 is moreover positioned so as to extend into the central passage 16 of the implantation tube 10 while protruding from its proximal end 12.

During an optional fifth step, when the envelope 30 comprises a net, the compressible member 20 can be re-humidified so as to soften it for the purpose of its withdrawal. For example, a catheter 50 can be introduced into the central passage 16 of the implantation tube 10 and into the central recess 26 of the compressible member 20 so as to inject a fluid, such as physiological serum. If necessary, the operator can use the possible markings or graduations present on the catheter 50 to facilitate and improve its positioning in the compressible member 20.

As a variant, the step of re-humidification can be accomplished prior to the installation of the implantation tube 10, for example using a syringe.

When the envelope 30 comprises a film, the re-humidification of the compressible member 20 can be optional in that said compressible member 20 is not contaminated thanks to the film that forms an interface with the nasal cavity of the patient. The compressible member therefore preserves its compression properties.

During a sixth step, the implantation tube 10 can be advanced progressively so as to receive the compressible member 20 and the envelope 30 in its distal end 14. Simultaneously, an operator pulls on the fastener 40 so as to avoid having the compressible member 20 move during the manipulation. In this manner, the compressible member 20 is progressively re-introduced and compressed in the implantation tube 10 and peels little by little from the walls of the nasal cavity, thus strongly limiting the risks of secondary hemorrhage.

The envelope 30, the implantation tube 10 and the fastener 40 thus allow avoiding a sudden and complete detachment over the entire length of the compressible member 20, which would be extremely painful for the patient.

If necessary, the use of an envelope 30 comprising a net having anticoagulant properties makes it possible to facilitate the detachment of the compressible member 20 by interrupting the continuity of the surface of the compressible member 20 likely to adhere to the walls of the nasal cavity, without however preventing the hemostatic phenomena, due to the small contact surface between the net 30 and the walls of the cavity.

When the envelope comprises a film 30 surrounded by a veil having hemostatic properties, only the film 30 and the compressible member 20 are re-introduced into the implantation tube 10, the veil remaining in place in the nasal cavity. The detachment of the film 30 and of the compressible member 20 is then facilitated in that the separation occurs beyond hemostasis. The veil having hemostatic properties can then be withdrawn separately and non-traumatically, using for example a gripper, in that it is substantially altered due to hemostasis.

If necessary, the reintroduction of the compressible member 20 into the implantation tube 10 is also facilitated by the flared shape 15 of the distal end 14 of the implantation tube 10.

When the totality of the compressible member 20 (sleeved into the envelope 30) is re-inserted into the implantation tube 10, the compressible member 20 is then in its compressed configuration.

During a seventh step, the implantation tube 10 can then be withdrawn.

Second Embodiment: Compression From the Inside of the Compressible Member

Figure 6:
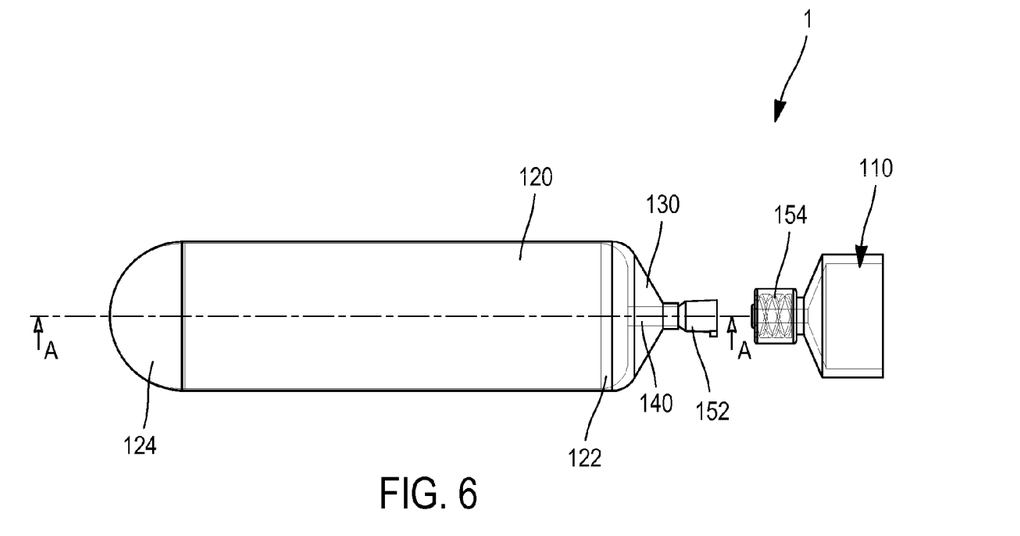
FIG. 6 is a partial side view of a first exemplary embodiment of a system for treating an epistaxis conforming to a second embodiment of the invention.
Figure 7:
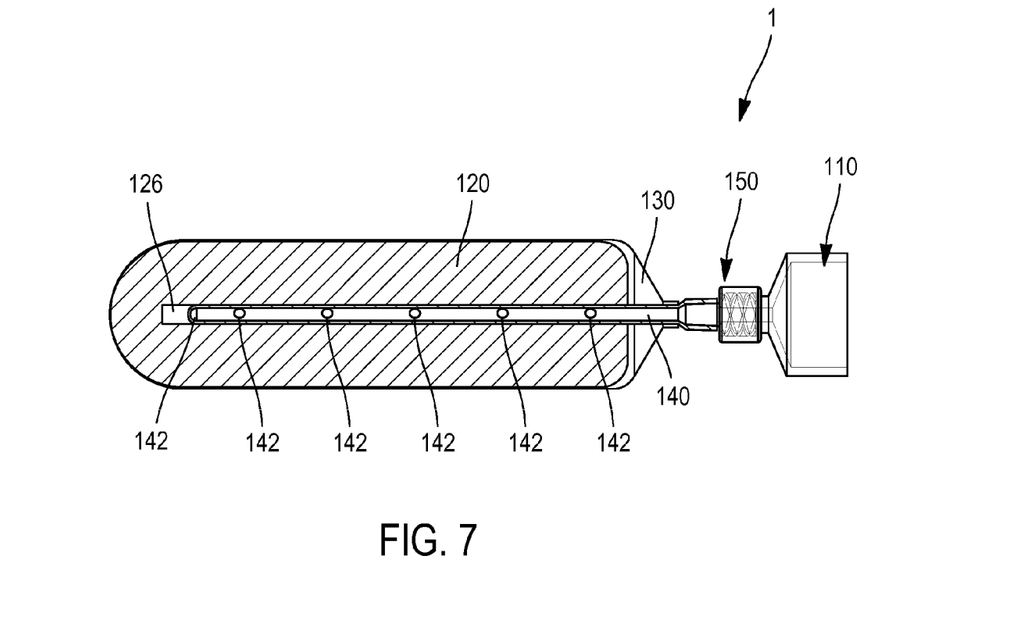
FIG. 7 is a section view of the treatment system of FIG. 6 along the axis A-A.
Figure 8:
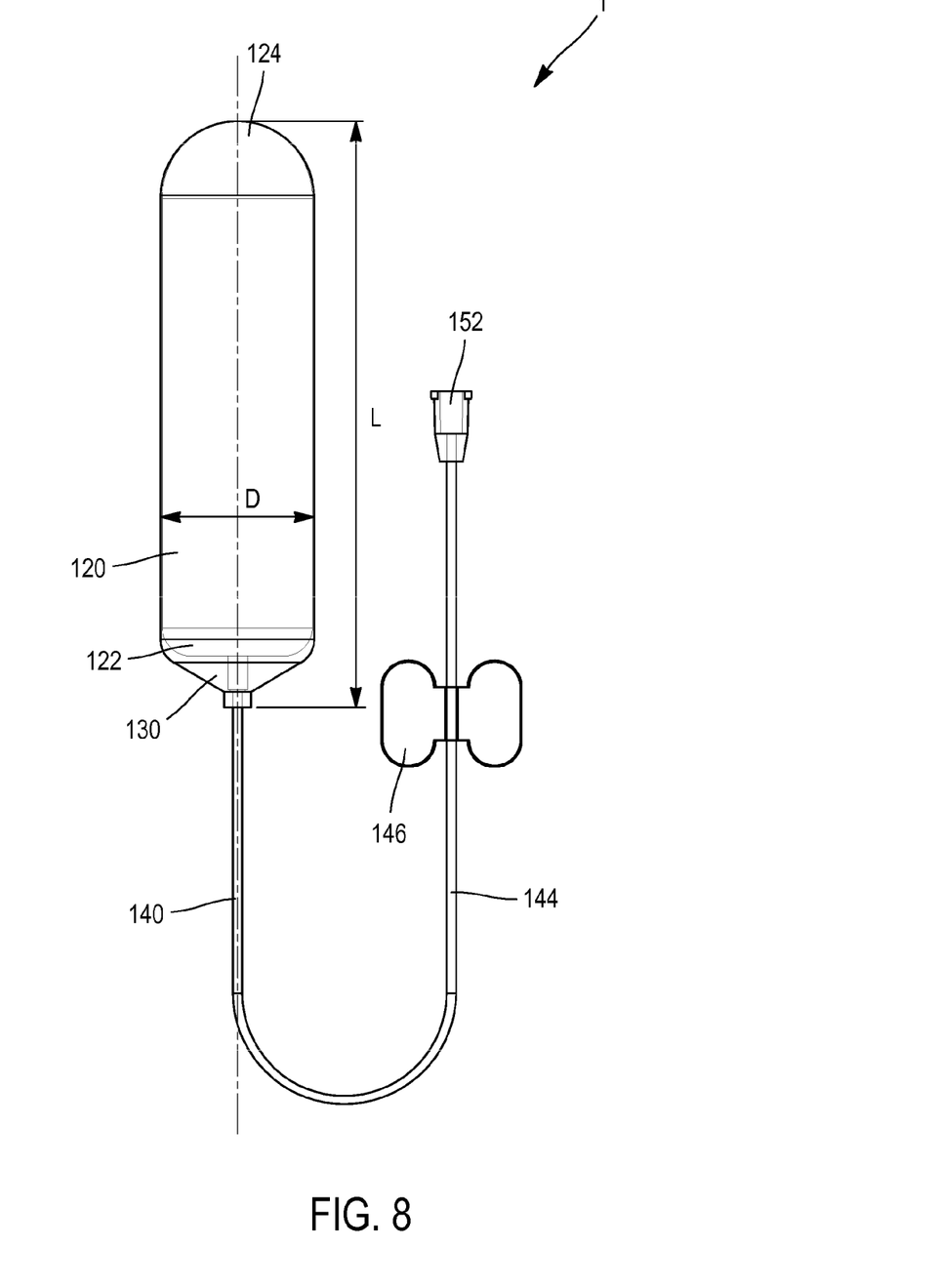
FIG. 8 is a side view of a second exemplary embodiment of a system for treating an epistaxis conforming to the second embodiment of the invention.

In this second embodiment, illustrated with reference to FIGS. 6 to 8, the compression device 110 is configured to aspirate air into the compressible member 120. To this end, the compression device 110 can in particular comprise a partial vacuum member, capable for example of reaching a vacuum in the compressible member 120 on the order of 450 mbar. Moreover, the envelope 130 is configured to sealingly enclose the compressible member 120 in order to allow this partial vacuum to be generated.

The compression device 110 can in particular comprise a syringe, for example a 50 mL syringe when the compressible member 120 has a length L of 10 cm for a diameter D of 2.8 to 2.9 cm.

As a variant, the compression device 110 could comprise a partial vacuum system 1 conventionally used in hospitals.

The envelope 130, which is sealed here, must be capable of resisting the pressure difference (with respect to the nasal cavity, which is at atmospheric pressure) created by the compression device 110 during the generation of a partial vacuum.

To this end, the envelope 130 can in particular comprise a flexible film which can be extensible or non-extensible. The envelope 130 can for example comprise a polymer film, such as a polyethylene, polyamide or polyurethane film. The envelope 130 can have a thickness comprised between a few microns and a hundred microns.

Unlike the systems of the prior art using an inflatable balloon, the pressurization of which is difficult to control, thus risking traumatizing the patient by applying forces that are too high on the walls of his nasal cavity, the system of the invention therefore proposes to apply a vacuum to the member 120 allowing the hemostatic phenomenon during the introduction or the extraction of the system and applying a pressure against the walls of the nasal cavity of the patient by simply allowing the body itself to assume a stable configuration close to its rest configuration.

In addition, during the introduction of the compressible member 120 into a nasal cavity, the member 120 is in a compressed configuration and is therefore rigid by comparison with an inflatable balloon (which is deflated, and therefore flexible, at the time of its introduction). The manipulation of the system 1 is therefore facilitated and more precise.

As indicated above, the compressible member 120 can comprise a foam. The foam being enclosed in a hermetic envelope 130, it is not necessary for it to have hemostatic properties. The foam can therefore be inert and be made of a material not having hemostatic properties.

On the other hand, the envelope 130 itself can be enclosed in a veil also having hemostatic properties if it is desired to confer hemostatic properties on the system 1, in that this veil is configured to come into contact with the walls of a nasal cavity. Such a veil can in particular be made of oxidized regenerated cellulose having hemostatic properties. The veil can then comprise a nonwoven veil having an acid pH of the Surgicel® type. It will be noted that this veil is, however, optional in that the compression force alone, applied by the compressible member 120 when it assumes its expanded configuration, allows a first hemostasis to be accomplished.

If necessary, the envelope 130 can be lubricated in order to facilitate the introduction and withdrawal of the system 1 in a nasal cavity of a patient.

The compressible member 120 has a distal end 124, configured to be placed at the back of a nasal cavity of a patient, and a proximal end 122 opposite to the distal end 124 at which is connected the compression device 110.

In order to facilitate the introduction of the compressible member 120 into a nasal cavity of a patient, the system 1 can further comprise a tube 140 or catheter, inserted into the compressible member 120 for the purpose of stiffening it. To this end, a central recess 126 can be formed between the proximal end 122 and the distal end 124 of the compressible member 120. The tube 140 is then housed in this central recess 126. The assembly formed by the compressible member 120 and the tube 140 is then rigid, in particular when the compressible member 120 is in the compressed configuration, which greatly facilitates its introduction into a nasal cavity (particularly in comparison with balloon system, which are flexible).

In one embodiment, the tube 140 is attached in the compressible member 120. If necessary, the tube 140 can be non-removable.

As a variant, the tube is hollow and is in fluid communication with the compression device 110. Through openings 142 are also formed in the wall of the tube 140 in order to allow the compression device 110 to aspirate air present in the compressible member 120 via the tube 140 and its openings 142. The through openings 142 extend preferably over a large portion of the length L of the compressible member 120, between its proximal end 122 and its distal end 124, which allows homogenizing the discharge or introduction of air when the compressible member 120 is brought into the compressed or expanded configuration. In this manner the compression and expansion of the compressible member 120 can be progressive and homogenous over the entire surface of the compressible member 120, thus reducing the trauma for the patient during its expansion (installation) and its compression (during withdrawal).

The tube 140 can have a length substantially equal to the length L of the compressible member 120 and protrude from said compressible member 120 at its proximal end 122.

As a variant, the tube 140 can have a greater length than that of the compressible member 120 and comprise a portion 144 configured to be attached to a zone of the body of the patient, when the compressible member 120 and the tube 140 are placed in a nasal cavity of said patient. It will be noted in fact that the compressible member 120 is configured to remain in place in a nasal cavity of a patient for approximately 48 hours. It is therefore preferable that, during this period, the patient is not at risk of embedding the compressible member 120 deeper and can, as much as possible, be comfortably installed. The Applicant has therefore noted that, by extending the tube 140 so as to attach it to the cheek or the side of the nose (for example) of the patient, the patient would have less risk of moving the compressible member 120 than when the tube 140 barely extended out from his nose.

If necessary, the extended portion 144 of the tube 140 which protrudes from the nose can be equipped with a fin 146 in order to facilitate attachment of this extended portion 144 to the body of the patient.

The system 1 can further comprise a lock 150 configured to allow the connection of the compression device 110 to the envelope 130 and thus allow the discharge or introduction of air into the compressible member 120. To this end, the lock 150 can in particular include a first attachment member 152, connected to the envelope 130 or to the tube 140, and a second complementary attachment member 154, connected to the compression device 110.

In the case where the system 1 comprises a tube 140, the first attachment member 152 can be attached to the end of the tube 140 which protrudes from the compressible member 120. The envelope 130 is then sealed hermetically in proximity to the proximal end 122 of the compressible member 120, either on the tube 140, or on the first attachment member 152, so as to form a sealed enclosure. For example, the envelope 130 can be sealed by gluing.

When the tube 140 is extended so as to protrude from the nose of the patient and to be attached to a zone of his body, the first attachment member 152 can be attached to the end of the extended portion 144 of the tube 140, at a distance from the compressible member 120. This configuration also allows the manipulation of the system 1 by an operator to be facilitated, the latter being freer in his movements during aspiration of air by means of the compression device 110. The envelope 130 is then sealed hermetically on the tube 140, at the outlet of the compressible member 120, so as to form a sealed enclosure (by gluing for example).

The first and the second attachment members 152, 154 can be conventional and comprise for example a system of the Luer type, or Luer lock.

The system 1 for treating an epistaxis conforming to this second embodiment can then be implemented as follows.

The implementation of this second embodiment will be detailed for a system 1 comprising a hemostatic veil and a tube 140, housed in a central recess 126 of the compressible member 120 and in fluid communication with the compression device 110. It will be understood, however, that the use of the hemostatic veil is optional.

In a first embodiment, the system 1 for treating an epistaxis can be supplied as a kit. The system 1 must then be assembled prior to its use.

To this end, the compressible member 120 is first enveloped or introduced into an envelope 130. At this assembly step, the compressible member 120 is in the deployed configuration. The compressible member 120 can, for example, comprise an inert foam with a length L comprised between 8 and 12 cm, typically on the order of 10 to 11 cm, and having a diameter D comprised between 2.5 and 3.0 cm, typically on the order of 2.8. to 2.9 cm.

A tube 140 including through openings 142 is then introduced into the central recess 126 of the compressible member 120. The tube 140 can for example have an outer diameter on the order of 2 to 3 mm and between 3 and 10 through openings 142 distributed over the portion of its length which is housed in the compressible member 120. The tube 140 is further equipped, at its free end, with an attachment member 152.

The envelope 130 can comprise a polyurethane film having a thickness of 50 microns.

The envelope 130 is then sealed, for example over a portion of the tube 140 which protrudes from the compressible member 120, by gluing for example.

A compression device 110, a syringe for example, comprising a complementary attachment member 154, is then connected to the attachment member 152 of the tube 140. The compression device 110 can then reduce the pressure (with respect to the ambient environment which is at atmospheric pressure) in the assembly formed from the compressible member 120 enclosed in the envelope 130 by aspiring the air contained from said assembly until the compressible member 120 achieves its compressed configuration. In the case of a syringe, it is sufficient for example for an operator to aspire the air by displacing the piston of the syringe.

Typically, for a compressible member 120 comprising foam described above, the operator can achieve a vacuum on order of 450 mbar. It will be noted that it is conceivable to achieve greater pressure in the compressible member: however, the foam would be less compressed, thus increasing the discomfort of the patient during the introduction of the wick.

Then the assembly formed from the envelope 130, the compressible member 120 and the tube 140 can be enveloped in a veil having hemostatic properties.

As a variant, the assembly formed from the tube 140 previously introduced into the compressible member 120 and enclosed hermetically in the envelope 130 can be pre-assembled and supplied as a kit to the operator, if necessary pre-packaged in the veil. It is then sufficient for the operator to connect the compression device 110, for example a syringe, to the tube 140 in order to reduce the pressure in the compressible member 120 and bring the compressible member 120 into its compressed position.

The syringe can be supplied with the kit which is then ready for use, or, as a variant, be separated from the kit (this variant being easier to contemplate when the connection is standardized, as a Luer or Luer Lock connection can be).

Then during a first step, the assembly (formed by the compressible member 120 in the compressed configuration, the tube 140, the envelope 130 and the veil), which is attached to the syringe, is brought and positioned in the nasal cavity of the patient so that the distal end 124 of the compressible member 120 is placed at the epistaxis. This introduction is facilitated by the presence of the tube 140, which allows the assembly to be stiffened without however increasing the bulk of the compressible member 120.

The compressible member 120 (as well as the tube 140, the envelope 130 and the veil) is then positioned with accuracy in the nasal cavity. In fact, the position of the compressible member 120 can be easily determined by the position of its distal end 124, which can be adjusted without risking injuring the patient in that the compressible member 120 is in the compressed configuration and therefor has reduced bulk.

During a second step, the compressible member 120 can be deployed in the nasal cavity. To this end, the compressible member 120 is brought from its compressed configuration to its expanded configuration, that is its stable configuration close to its rest position (the compressible member 120 having shape memory).

In the case of a compression device 110 comprising a syringe, it is sufficient for example to disconnect the syringe, the compressible member 120 progressively resuming its shape thanks to the passive aspiration of air via the through openings 142 and the tube 140. As a variant, the operator can re-inject the previously aspirated air into the compressible member 120 by pressing on the piston of the syringe. Preferably, the re-injection is carried out progressively so as not to traumatize the patient.

In any case, the compressible member 120 is deployed progressively thanks to the through openings 142 formed along the tube 140, which reduces the trauma to which the patient is subjected, the compressible member 120 not being moved at any time during its expansion. Moreover, by adopting its expanded configuration, the compressible member 120, which is enclosed in the envelope 130, and if necessary the veil having hemostatic properties, comes into contact with the walls of the nasal cavity.

The compression device 110 can then be withdrawn. If necessary, when the tube 140 comprises an extended portion, possibly equipped with a fin 146, said extended portion can be attached to the skin of the patient.

A hemostatic phenomenon can then take place, thanks on the one hand to the compression force applied by the compressible member 120 to the walls of the nasal cavity, and on the other hand to the hemostatic properties of the hemostatic veil which surrounds the envelope 130 and the compressible member 120.

At the end of the hemostatic phenomenon, the assembly formed by the compressible member 120, the envelope 130, the tube 140 and the veil can then be withdrawn.

For this purpose, during a third step the compression device 110, a syringe for example, can be connected to the assembly. For example, the attachment member 154 of the syringe can be connected to the corresponding attachment member 152 of the tube 140.

During a fourth step, the pressure in the compressible member 120 is reduced so as to bring the compressible member 120 back into its compressed configuration. Typically, for a compressible member 120 comprising foam described above, the operation can again attain a vacuum on the order of 450 mbar by moving the piston of the syringe so as to aspire the fluids (particularly air) enclosed in the foam.

The partial vacuum generated in the compressible member 120 is, once again, progressive. Moreover, the air is aspirated over the entire length of the compressible member 120 due to the through openings 142 formed in the tube 140. In this manner, the compressible member 120 is brought progressively into its compressed configuration, detaching itself slowly in a direction substantially perpendicular to the walls of the nasal cavity, as opposed to the tangential and total detachment which was generally obtained with conventional treatment systems.

During a fifth step, when the compressible member 120 (enclosed in the envelope 130 and the veil) has reached its compressed configuration, it can then be extracted from the nasal cavity.

The invention claimed is:

1. A system for treating an epistaxis, comprising:
a compressible member having a compressed configuration, in which the compressible member is compressed and is configured to be introduced into a nasal cavity of a patient, and an expanded configuration, in which the compressible member is deployed and is configured to come into contact with walls of the nasal cavity of the patient, wherein the compressible member comprises a shape-memory material such that the compressible member passively expands to the expanded configuration; and
an envelope configured to hermetically envelop the compressible member so as to form a sealed enclosure,
a hollow compression device for compressing the compressible member and the envelope to bring the compressible member into the compressed configuration.

2. The system according to claim 1, wherein the envelope comprises a flexible film.

3. The system according to claim 2, wherein the envelope comprises a film having a thickness of up to one hundred microns and is made of at least one of the following materials: polyethylene, polyurethane.

4. The system according to claim 1, wherein the compression device comprises a syringe or a partial vacuum member.

5. The system according to claim 1, wherein the compressible member has a proximal end and a distal end, a central recess being formed between the proximal end and the distal end of the compressible member and the system further comprising a tube housed in the central recess.

6. The system according to claim 5, wherein the tube comprises through openings between the proximal end and the distal end of the compressible member and is configured to put the compressible member and the envelope into fluid communication with the compression device to allow progressive compression and expansion of the compressible member over an entire length of the compressible member.

7. The system according to claim 5, further comprising a lock comprising a first attachment member, attached to a proximal end of the tube and a second complementary attachment member attached to the compression device.

8. The system according claim 5, wherein the tube protrudes from the compressible member and comprises a fin configured to be attached to a zone of the body of a patient.

9. The system according to claim 1, wherein the envelope has is planar sheet or a sleeve.

10. The system according to claim 1, further comprising a veil having hemostatic properties covering the envelope.

11. the system according to claim 1, wherein the shape-memory material comprises a foam.

12. The system of claim 1, wherein the compression device is configured to reduce a pressure in the compressible member and the envelope.

13. The system of claim 12, wherein the compression device includes a syringe.

14. A system for treating an epistaxis, comprising:
a compressible member having a proximal end and a distal end, wherein the compressible member has a compressed configuration, in which the compressible member is compressed and is configured to be introduced into a nasal cavity of a patient, and an expanded configuration, in which the compressible member is deployed and is configured to come into contact with walls of the nasal cavity of the patient,
an envelope configured to hermetically envelop the compressible member so as to form a sealed enclosure,
a hollow compression device configured to reduce a pressure in the compressible member and the envelope and bring the compressible member into the compressed configuration,
a tube housed in a central recess of the compressible member that extends between the proximal end and the distal end of the compressible member, and
a lock comprising a first attachment member, attached to a proximal end of the tube and a second complementary attachment member attached to the compression device such that the compression device is attached in proximity to the proximal end of the compressible member.

15. The system of claim 14, wherein the compressible member comprises a shape- memory material.

16. The system of claim 15, wherein the shape-memory material of the compressible member is arranged such that the compressible member passively expands to the expanded configuration.

17. The system of claim 14, wherein the envelope comprises a film.

18. A system for treating an epistaxis, comprising:
a compressible member having a proximal end and a distal end, wherein the compressible member has a compressed configuration, in which the compressible member is compressed and is configured to be introduced into a nasal cavity of a patient, and an expanded configuration, in which the compressible member is deployed and is configured to come into contact with walls of the nasal cavity of the patient,
an envelope configured to hermetically envelop the compressible member so as to form a sealed enclosure,
a hollow compression device configured to reduce a pressure in the compressible member and the envelope and bring the compressible member into the compressed configuration,
a tube housed in a central recess of the compressible member that extends between the proximal end and the distal end of the compressible member, wherein the tube protrudes from the compressible member and comprises a fin configured to be attached to a zone of the body of a patient.

* * * * *